US00PP10269P

United States Patent [19]

Button

[11] Patent Number: Plant 10,269

[45] Date of Patent: Mar. 3, 1998

[54] AGLAONEMA PLANT NAMED 'PATRICIA'

[75] Inventor: Richard J. Button, Miami, Fla.

[73] Assignee: Sunshine Foliage World, Zolfo Springs, Fla.

[21] Appl. No.: 733,733

[22] Filed: Oct. 18, 1996

[51] Int. Cl.[6] ..... A01H 5/00

[52] U.S. Cl. ..... Plt./88.1

[58] Field of Search ..... Plt./88.1

*Primary Examiner*—Howard J. Locker

*Assistant Examiner*—Kent L. Bell

*Attorney, Agent, or Firm*—C. A. Whealy

[57] ABSTRACT

A new and distinct cultivar of Aglaonema named 'Patricia' particularly characterized by its short, compact, and well-branched growth habit and its silver green lanceolate leaves with dark green markings.

2 Drawing Sheets

The present invention relates to a new and distinct cultivar of Aglaonema plant, botanically known as *Aglaonema hybrida*, and hereinafter referred to by the cultivar name 'Patricia'.

The new cultivar is a product of a planned breeding program conducted by the inventor in Miami, Fla. The new cultivar originated from a cross by the inventor between the two unidentified Aglaonema selections. The cultivar 'Patricia' was discovered and selected by the inventor as a plant within the progeny of the stated cross in a controlled environment in Miami, Fla.

Asexual propagation of the new cultivar at Zolfo Springs, Fla., has shown that the unique features of this new Aglaonema plant are stable and reproduced true to type in successive generations of asexual propagation.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice.

The following traits have been repeatedly observed and are determined to be the unique characteristics of 'Patricia'. These characteristics in combination distinguish 'Patricia' as a new and distinct cultivar:

1. Plants of the new Aglaonema are short with a freely branching, dense, compact and upright growth habit.

2. Adaxial leaf surfaces of plants of the new Aglaonema are predominantly silver green in color with a dark green midrib and dark green blotches which extend from the midrib to the leaf margin.

3. Leaves of plants of the new Aglaonema are lanceolate in shape and distinctly tapered to a point at the apex.

Plants of the new Algaonema can be compared to plants of the Aglaonema cultivar 'Silver Queen' (not patented). Plants of the new Aglaonema differ from plants of the cultivar 'Silver Queen' in the following characteristics:

1. Plants of the new Aglaonema grow slower than plants of the cultivar 'Silver Queen'.

2. Plants of the new Aglaonema are more compact, more freely branching and denser than plants of the cultivar 'Silver Queen'.

3. Unlike leaves of plants of the cultivar 'Silver Queen', mature leaves of plants of the new Aglaonema are lanceolate in shape and almost entirely silver green in color with contrasting dark green markings.

The accompanying colored photographs illustrate the overall appearance of the new cultivar, showing the colors as true as it is reasonably possible to obtain in colored reproductions of this type.

The first photograph comprises a top perspective view of a typical single plant of 'Patricia' in a 26-cm container about 20 months after planting.

The second photograph comprises a cover-up view of the abaxial (left) and adaxial (right) surfaces of a mature leaf and illustrates the detail of the leaf color pattern.

Leaf colors in the photographs may appear different from the actual colors due to light reflectance.

In the following description, color references are made to The Royal Horticultural Society Colour Chart except where general terms of ordinary dictionary significance are used.

Botanical classifications: *Aglaonema hybrida* cultivar 'Patricia'.

Parentage:

*Seed or female parent.*—Unidentified Aglaonema selection.

*Pollen or male parent.*—Unidentified Aglaonema selection.

Propagation: By divisions or by tissue culture.

Plant description:

*Plant shape.*—Upright and outwardly spreading, symmetrical, dense and compact.

*Growth habit.*—Erect when young, becoming outwardly spreading as leaves develop.

*Plant size.*—Height: Approximately 39 to 44 cm from the soil surface to top of leaf canopy. From the soil level to the petiole apex of the last unrolled leaf, approximately 12.5 to 15.5 cm. Width: Approximately 71 to 80 cm.

*Root description.*—Thick white roots with fine laterals.

*Stem description.*—Upright. Diameter: Approximately 1.5 to 1.8 cm, 5 cm above the soil surface. Internode length: Approximately 1.2 to 1.6 cm, 3 cm above the soil surface. Color: 147A with areas of 160C.

*Petiole description*—The following description is based on the fourth expanded leaf from the apex. Growth pattern: The petiole has fleshy edges extending from the midrib that are referred to as wings. Wings extend from the base of the petiole to approximately 1.4 to 2.7 cm below the base of the leaf. The wings are about 2 to 4 mm wide midway from the petiole base to the wing apex. The wing apex is acute. The petiole follows the stem axis but diverges from the axis about 8.2 cm to 11.0 cm from the leaf base, forming a horizontal distance from the vertical axis of the stem to the leaf base of 2.7 cm to 4.3 cm. The oldest petioles are marked with thin callused striations which encircle the petiole between the top of the wing and the base of the leaf. Dimensions: The petiole is often curved from its base to the tip of the wings, and curved or somewhat twisted between the wing apex and the base of the leaf. The petiole is approximately 4 mm to 5 mm in diameter midway between the wing apex and the base of the leaf. The petiole is 10 cm to 11.5 cm in length from its base to the base of the leaf. Color: The petiole wings and petiole midrib are 147A with occasional spots of 147B/147C.

*Leaf description.*—Axillary breaks: There are approximately 15 axillary breaks with at least one leaf expanded. First leaves will show true color and color pattern. Growth Pattern: The leaf is lanceolate in shape with an acute apex and an obtuse base. The leaf margin is entire. The leaf blade is asymmetric with the side of the leaf unrolling first having less surface area than the side unrolling last. The leaf is oriented parallel to the stem axis at the time of full unrolling, changing to approximately 30 to 40 degrees from the vertical stem axis as more leaves unroll above it. The leaf blade is flat from the midrib to the margin and the midrib is straight. The margin is flat or slightly wavy. Dimensions: For the pot size and growing time indicated, the largest leaves are approximately 23.0 cm to 25.5 cm long and approximately 6.0 cm to 7.2 cm wide. Average sized leaves are approximately 20.0 cm to 22.1 cm long and approximately 5.4 cm to 5.9 cm wide. The leaf blade is relatively thick and leathery in texture with a glossy surface. Midrib: The midrib is thick and prominent, recessed on the adaxial surface and prominent on the abaxial surface. Primary veins: The primary veins are sunken into the adaxial surface and are slightly prominent on the abaxial surface. The primary veins are the same color as the tissue surrounding them. The leaf blade is convex between the primary veins. Pattern: The upper leaf surfaces are predominantly silver green in color. The midrib is dark green. The leaf blade is marked with dark green blotches which extend from the midrib toward the leaf margin. The leaf margin is streaked and spotted with dark green. The lower leaf surface is medium green, with slightly darker green chevron-shaped markings which extend from the midrib toward the margin. Color: Newly opened leaf, adaxial surface: 191B. Midrib: Dark green markings. Leaf margin: 147A. Newly opened leaf, abaxial surface: 147C with chevron-shaped markings, 147B. Midrib: Greener than 147C. Mature leaf, adaxial surface: 191A with 148B/148C. Midrib: Dark green markings. Leaf margin: 147A. Mature leaf, abaxial surface: 147B/147C with chevron-shaped markings, 147B. Midrib: Greener than 147B.

*Inflorescence.*—Typical of Aglaonema, no commercial significance.

General Observations

Plants of the Aglaonema cultivar 'Patricia' are relatively short-growing having a freely-branching, dense, compact and upright growth habit. The adaxial leaf surfaces are predominantly silver green in color with contrasting dark green markings along the leaf blade midrib and extending towards the leaf margin. The leaves are lanceolate in shape and distinctly tapered to a point at the apex. These combined characteristics make 'Patricia' a distinct and unique new cultivar.

It is claimed:

1. A new and distinct cultivar of Aglaonema plant named 'Patricia', as illustrated and described.

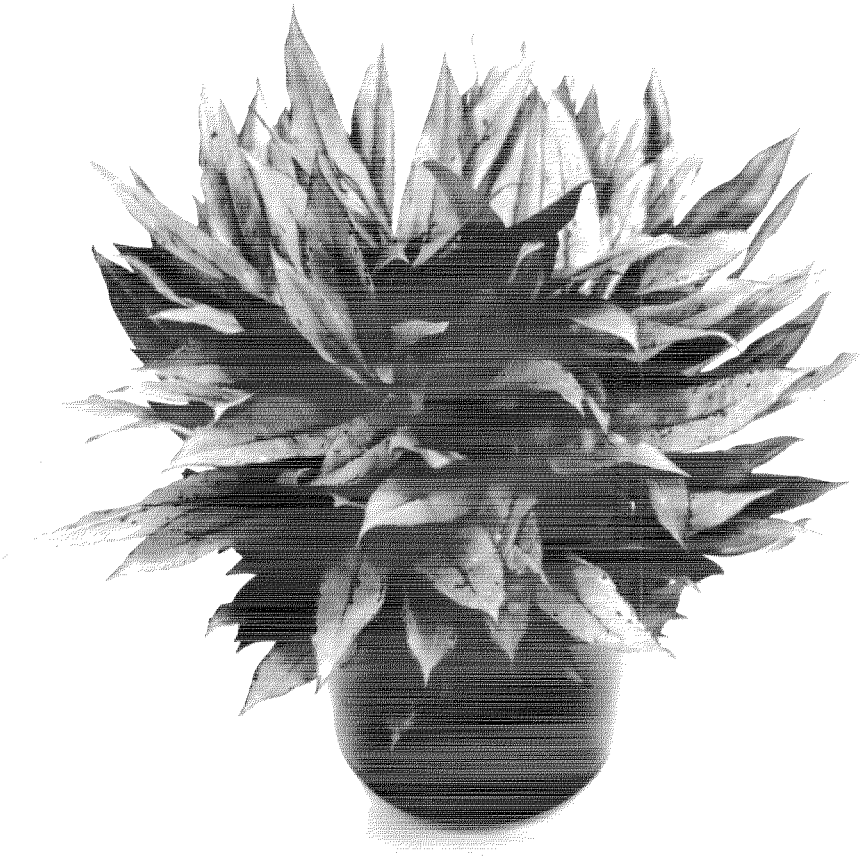

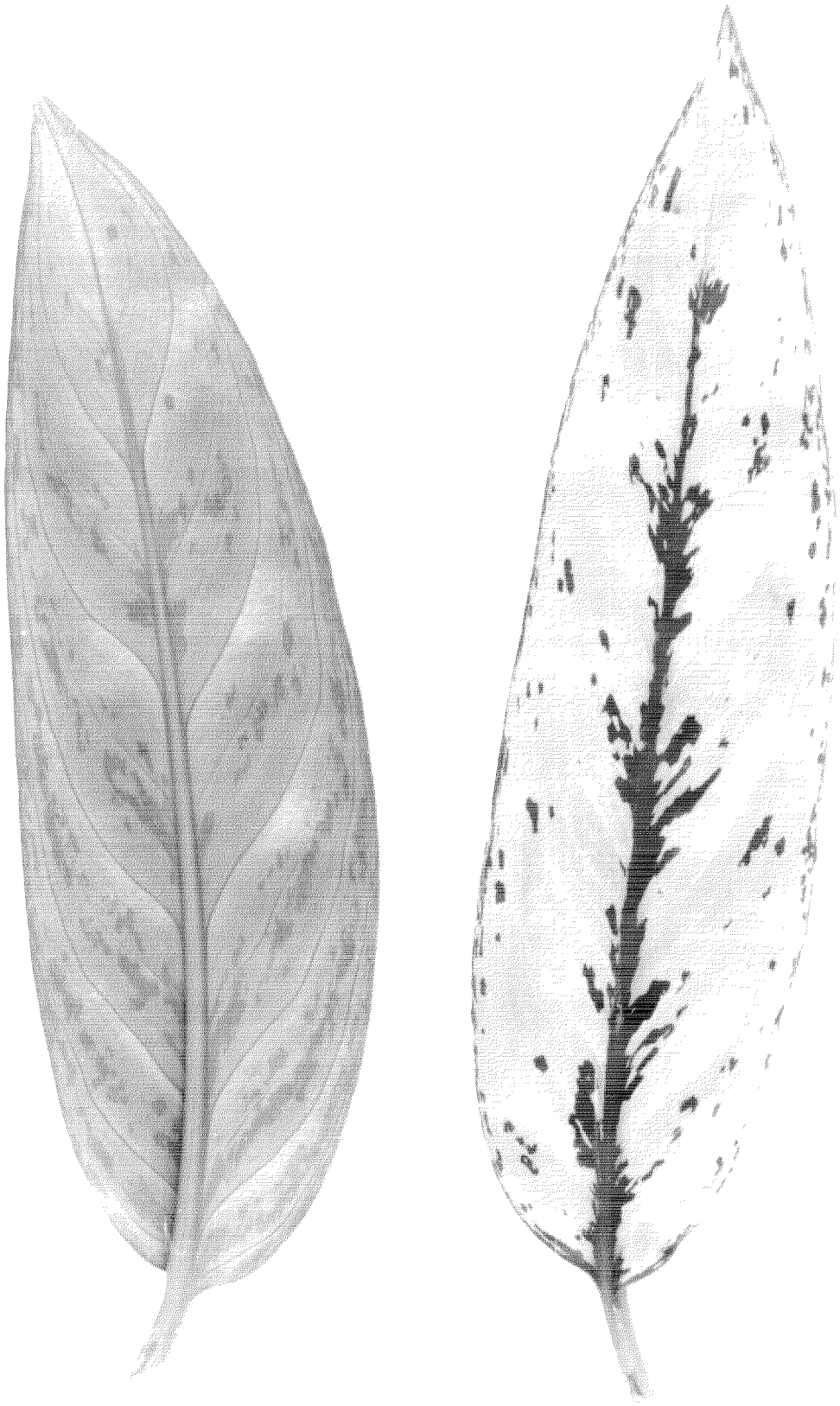

* * * * *